United States Patent [19]

Spears

[11] Patent Number: 4,577,636
[45] Date of Patent: Mar. 25, 1986

[54] METHOD FOR DIAGNOSIS OF ATHEROSCLEROSIS

[75] Inventor: J. Richard Spears, Boston, Mass.

[73] Assignee: The Beth Israel Hospital Association, Boston, Mass.

[21] Appl. No.: 574,682

[22] Filed: Jan. 27, 1984

Related U.S. Application Data

[63] Continuation-in-part of Ser. No. 443,958, Nov. 23, 1982, Pat. No. 4,512,762.

[51] Int. Cl.[4] ............................ A61B 6/00; A61B 5/02
[52] U.S. Cl. .................................. 128/654; 128/659; 128/666
[58] Field of Search ............... 128/653, 654, 656, 665, 128/666, 303.1; 604/20, 21, 49-53

[56] References Cited

U.S. PATENT DOCUMENTS

| | | | |
|---|---|---|---|
| 3,494,354 | 2/1970 | Yokota et al. | 128/6 |
| 3,557,783 | 1/1971 | Castner | 128/172.1 |
| 3,661,148 | 5/1972 | Kolin | 128/668 |
| 4,266,549 | 5/1981 | Kimone | 128/303.1 |
| 4,315,512 | 2/1982 | Fogarty | 128/344 |
| 4,323,071 | 4/1982 | Simpson et al. | 128/343 |
| 4,336,809 | 6/1982 | Clark | 128/665 |
| 4,384,584 | 5/1983 | Chen | 604/28 |
| 4,459,990 | 7/1984 | Barnea | 128/656 |

OTHER PUBLICATIONS

Lancet, Jan. 6, 1979, pp. 9-11.
British Medical Journal, London, Sat. 28, May 1977, p. 1371.
Annals New York Academy of Sciences, 276, 1976, pp. 96-100.
Scientific American, 236, Feb. 1977, pp. 74-84.
Aqueous Peroxyoxalate Chemiluminescence, Final Report to the Office of Naval Research, Contract N00014-77-C-0634, A. Mohan et al., Discovery Research Department, Chemical Research Div., American Cyanamid Company, Bound Brook, N.J., pp. 1-156 (Jan. 1982).
"Atherosclerosis", H. Wolinsky, Cardiovascular Diseases (U.S.A.) vol. XIV, pp. 1218-1222.
"The Photodynamic Properties of a Particular Hematoporphyrin Derivative", R. Lipson et al., Archives of Dermatology (U.S.A.), 82:76/508-84/516 (1960).
R. Lipson et al., "Hematoporphyrin Derivative for Detection and Management of Cancer", Cancer (U.S.A.), 20:2255-2257 (Dec. 1967).
R. Lipson et al., "The Use of a Derivative of Hematoporphyrin in Tumor Detection", Journal of the National Cancer Institute (U.S.A.) 26:1-8 (Jan. 1961).
D. Sanderson et al., "Hematoporphyrin as a Diagnostic Tool", (U.S.A.) Cancer, 30:368-1372 (Nov. 1972).
Cancer Therapy Abstracts (U.S.A.), 79-0299, T. Dougherty, "Photoradiation in the Treatment of Recurrent Breast Carcinoma", p. 69 (1979).
Cancer Therapy Abstracts (U.S.A.), 79-0463, T. Sory, "Photodynamic Killing of Retinoblastoma Cells with Hematoporphyrin and Light", pp. 160-161 (1979).
Cancer Therapy Abstracts (U.S.A.), 79-2363, J. Moan, "The Mechanism of Photodynamic Inactivation of Human Cells in Vitro in the Presence of Haematoporphyrin", pp. 735-736 (1979).
F. Gollan et al., "Oxygen Transport of Colloidal Fluorocarbon Suspensions in Asanguineous Rabbits", American Journal of Physiology (U.S.A.), 229:1045-1049 (Oct. 1975).
K. Kanter et al., "Superiority of Perfluorocarbon Cardioplegia Over Blood or Crystalloid Cardioplegia", Circulation (U.S.A.), vol. 64, Supplement II, pp. 11-75-1-1-80 (Aug. 1981).
"Fluorescence of Experimental Atheromatous Plaques with Hematoporphyrin Derivative", J. Richard Spears, Juan Serur, Deborah Shropshire, and Sven Paulin, J. Clin. Invest., 71:395-399 (1983).
"In Vivo Coronary Angioscopy", J. Richard Spears, H. John Marais, Juan Serur, Oleg Pomerantzeff, Robert P. Geyer, Robert S. Sipzener, Ronald Weintraub, Robert Thurer, Sven Paulin, Richard Gerstin, William Grossman, J. Am. Coll. Cardiol., 1:1311-1314 (1983).

Primary Examiner—William G. Wright
Attorney, Agent, or Firm—Pahl, Lorusso & Loud

[57] ABSTRACT

Method for diagnosis of the presence of atherosclerosis plaques. The method comprises injection of a hematoporphyrin which is selectively absorbed by atheromotous plaques. The hematoporphyrin is then subjected to light causing it to fluorese and the fluorescence is used to diagnose the presence of the plaques.

10 Claims, No Drawings

METHOD FOR DIAGNOSIS OF ATHEROSCLEROSIS

CROSS-REFERENCE TO A RELATED APPLICATION

This application is a continuation-in-part of Application No. 443,958 now U.S. Pat. No. 4,512,762 entitled "Method of Treatment of Atherosclerosis and A Balloon Catheter for Same", filed on Nov. 23, 1982, the teachings of which are incorporated herein by reference.

BACKGROUND OF THE INVENTION

Atherosclerosis is a disease wherein fatty substances (lipids), hereinafter referred to as atheromatous plaques, form deposits in and beneath the intima which is the innermost tissue lining arteries and veins. Clinical symptoms occur because the mass of the atherosclerotic plaque reduces blood flow through the involved artery, comprising tissue or organ function.

In the co-pending patent application Ser. No. 443,958 now U.S. Pat. No. 4,512,762, a treatment for artherosclerosis is disclosed. This treatment is based on the discovery that hematoporphyrin derivative (HPD) selectively accumulates in atheromatous plaques and not in the adjacent normal tissue. These plaques can be treated or removed by photoactivating the porphyrin(s) with visible light, which apparently causes the release of singlet oxygen which in turn damages the atheromatous plaque cell. This cytotoxic mechanism is discussed in "Identification of Singlet Oxygen As The Cytotoxic Agent in Photoinactivation of A Murine Tumor." by K. R. Weishaupt, C. J. Gromer, and T. J. Dougherty, *Cancer Research*, 36:2326–2329 (1976).

Photoactivation of the HPD, as taught by patent application Ser. No. 443,958 now U.S. Pat. No. 4,512,762, can be accomplished by either of two different techniques. With one technique, the patient is catheterized with a light-emitting catheter inserted into the diseased artery until the light-emitting portion of the catheter is adjacent the atheromatous plaque. With the alternative technique, light-emitting liquid, such as the aqueous peroxyalate chemiluminescent system made by American Cyanamid Co., is injected into the vascular tree so that the liquid, which mixes freely with the blood or a blood replacement, perfuses the diseased artery and photoactivates the absorbed hematoporphyrin.

The referenced application teaches an invasive means for reducing or removing atheromatous plaques. No conventional invasive test is currently available which can be used to reliably image or quantitate atheromatous plaques. Arteriography is a definitive procedure for determining the extent of human encroachment by plaques, but cannot be used to image the plaques per se. During a catherization procedure, an ultrathin fiberoptic catheter (an angioscope) is introduced into the arterial tree. The lumen may be visualized directly by displacing the blood with an optically clear medium such as one of the presently available perfluorocarbon-containing blood replacements which provide both oxygen transport and maintain oncotic pressure. Demarcation between the artheromatous plaque and the normal artery wall is ambiguous, however, because the luminal surface of both tissues is the same whitish color. A technique for direct visualization of the blood vessel walls is disclosed in "In Vivo Coronary Angioscopy" by J. Richard Spears, H. John Marais, Juan Serur, Oleg Pomerantzeff, Robert P. Geyer, Robert S. Sipzener, Ronald Weintraub, Robert Thurer, Sven Paulin, Richard Gerstin and William Grossman, *J. Amer. College of Cardiology*, 1(5):1311–1314(1983).

Noninvasive techniques for detecting or defining atheromatous plaques are also quite limited. Ultrasound can be used to detect lumen encroachment by atheromatous plaques in the carotid artery, fluoroscopy can be used to identify plaques if they contain calcium deposits, and NMR can occasionally be used to identify plaques. None of these is a very reliable means for the noninvasive imaging of atheromatous plaques. As a result, currently used non-invasive tests for atherosclerotic coronary artery disease are based solely on the physiological consequences of lumen encroachment by the atheromatous plaques. Such tests include ECG, ECG stress testing, thallium perfusion imaging, and radionuclide ventriculography. A severe stenosis (approximately 70% diameter reduction) must be present, however, before an abnormality is detected by these tests.

The primary reason that atheromatous plaques cannot be reliably detected by the use of currently available noninvasive techniques is that atheromatous plaques do not differ significantly from surrounding tissues in any of the physio-chemical properties which alter the signals detected by the techniques.

It is therefore an objective of the present invention to provide a means for detecting, imaging, or quantifying atheromatous plaques which can be used with both invasive and noninvasive techniques.

SUMMARY OF THE INVENTION

In accordance with the present invention, the detection of the selective absorbtion of porphyrin(s) by atheromatous plaques can be used to image, localize, or quantify atheromatous plaques. The porphyrin(s) generate a signal which differentiates the plaque from the adjacent normal tissue.

Various types of signals are possible. Chemically unaltered porphyrins fluoresce when exposed to ultraviolet light and the fluorescence may be detected using invasive means at the time of surgery, postmortem examination, or during a catheterization procedure. Chemically altered porphyrins, absorbed by atheromatous plaques, may be detected using non-invasive techniques. Radiolabeled porphyrins may be detected using radionuclide scintographic techniques. Porphyrins labelled with short-lived tracers may be detected by Positron Emission Tomography (PET). Porphyrins labelled with radio-opaque markers may be used to visualize atheromatous plaques fluoroscopically. Porphyrins incorporating short-lived isotopes within their structures can be detected by nuclear magnetic resurance (NMR). Other means may be used where the presence of the porphyrin increases the measured signal-to-noise ratio between normal and diseased tissues.

The absorbtion of these porphyrins by the atheromatous plaques may be increased and their detection enhanced by binding antibody specific for components of the plaques to the porphyrins.

DESCRIPTION OF THE PREFERRED EMBODIMENT

In one embodiment of the present invention, a solution of porphyrins is injected into a peripheral vein from which it disseminates throughout the vascular system. The dosage depends on the purity and chemical form of the porphyrin and the degree of absorbtion expected. The most commonly used porphyrin is hematoporphyrin, which may be in purified form or mixed with other porphyrins. Other porphyrins not present in HPD, such as uroporphyrin I dihydrochloride, which may selectively localize within atheromatous plaques, may be used. For the purposes of this invention, "porphyrins" is defined as a solution containing one or more of these porphyrins.

When using hematoporphyrin derivative (HPD), available from Oncology Research and Development, as described in the copending patent application Ser. No. 443,958, the usual dosage is between 2.5 mg hematoporphyrin/kg body weight and 10 mg hematoporphyrin/kg body weight.

Other more highly purified hematoporphyrin preparations are now commercially available. These include Dihematoporphyrin ether (DHE) and Photofrin II, produced by Photofrin Medical, Inc.

The injected porphyrin is selectively absorbed into the atheromatous plaques, with the peak concentration occurring within 24 hours. The presence of the porphyrin in the tissue may be detected within a few hours after injection. The presence of the porphyrin in the tissue may persist for several days to two weeks.

Means for detection of the chemically unaltered porphyrin is primarily by fluorescence of the compound when it is exposed to ultraviolet light in the range of 400 to 410 nm. This fluorescence can only be detected by invasive means such as catherization, surgery, and post-mortem examination.

Catheterization is accomplished by use of an ultrathin fiberoptic catheter (an angioscope), such as the one described in the article "In Vivo Angioscopy", *J. Amer. College of Cardiology* 1(5):1311–1314. For fluoroscopy, an ultraviolet light would be used in place of the visible light.

Because of the precise imaging by fluorescence of porphyrin containing plaques, there is a decreased chance of vessel wall perforation at the time of laser vaporization of the plaques. The difference in fluorescence between normal tissue and atheromatous plaques is quite striking. A comparison was made in rabbit aortas and reported in "Florescence of Experimental Atheromatous Plaques with Hematoporphyrin Derivative" by J. Richard Spears, Juan Serur, Deborah Shopshire, and Sven Paulin, *J. Clin. Invest.* 71:395–399 (February 1983), the teachings of which are incorporated herein by reference. The only possible disadvantage to this technique is that the patient may develop a skin photosensitivity following injection of a hematoporphyrin solution. This appears to be due to impurities in the hematoporphyrin solution and persists for less than a week.

In another embodiment of the present invention, the porphyrin is labelled with a radioactive isotope prior to injection and the relative concentration of the porphyrin measured using radionuclide scintographic techniques.

Isotopes suitable for use as labels include those which can be substituted within the porphyrin ring such as copper, $^{64}Cu$, those molecules which make up the ring such as carbon and hydrogen, $^{14}C$ and $^{3}H$, and those which can be attached by means of side groups, such as iodine, $^{125}I$. The porphyrin may also be labelled by attaching radioactively labelled proteins to the porphyrin side groups. The copper isotope, $^{64}Cu$, has an advantage over radioisotopes such as $^{14}C$ and $^{3}H$ in that it has a very short half-life, twelve hours, so the patient is not exposed to radioactivity for a long period of time.

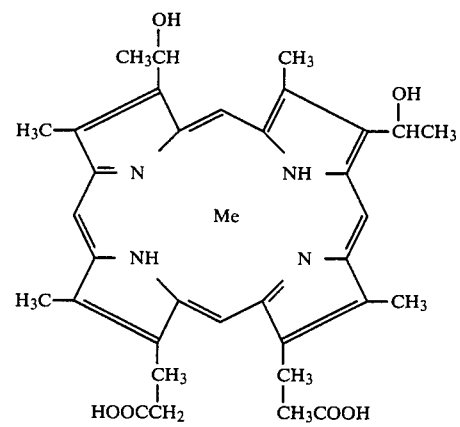

Hematoporphyrin with metal substituted porphyrin ring.

Iodine, $^{125}I$, has an additional advantage in that it is radio-opaque, and can be used as a contrast media for X-ray detection.

An example of X-ray detection, Digital Subtraction Angiography (DSA) is presently used with contrast medias in order to diagnose diseases of blood vessels of the brain and chest. In this procedure, an X-ray is made of the area of the body containing the blood vessels prior to injecting the contrast media. An X-ray taken after injection of contrast media is compared with the first X-ray and a computer used to construct an image of the blood vessels. Iodine-labelled porphyrin absorbed by atheromatous plaques can be used to show the location and quantity of plaques within these imaged blood vessels by increasing the low level contrast.

In yet another embodiment of the present invention, porphyrins incorporating isotopes within their structure may be detected using Positron Emission Tomography (PET). The Positron Emission Tomograph records the human body's metabolism by measuring traces of "nuclear annihilations" in body tissue. A patient receives short-lived tracers which emit particles called "positrons" which collide with electrons less than a few millimeters away to produce bursts of energy that detectors record. As these collisions occur repeatedly, the detectors build up a map of the location of the tracer chemical or the location where it is being metabolized.

Examples of tracers which may be used with PET include $^{68}Gallium$, $^{11}CO$, $^{13}NH_3$, and $^{11}C$-glucose.

In a similar embodiment of the present invention, absorbtion of substituted porphyrins is detected using Nuclear Magnetic Resonance (NMR) spectroscopy. With the NMR technique, the patient is placed within an extremely powerful magnetic field and encircling coils pulse the body with radio waves. Different kinds of atoms in the body re-emit radio signals in response. A computer processes the signals to form images of the body.

Examples of molecules that can be incorporated within the porphyrin ring for detection by NMR include maganese, iron, Gadolinium, Chromium, cobalt, nickel, silver, and europium.

The absorbtion of the porphyrin greatly enhances the signal measured by NMR. When an excised plaque was measured by NMR, the proton signals $T_1$ and $T_2$ were 450 milliseconds and 86 milliseconds, respectively. After the plaques were soaked in a porphyrin-maganese solution, the $T_1$ and $T_2$ signals were 70 milliseconds and 2.5 milliseconds, respectively. Some adaptations of the dosage, type of incorporated metal, etc., may have to be made for the technique to work as well in an in vivo situation. Unfortunately, once a metal has been incorporated into the hematoporphyrin, the compound no longer fluoresces so the NMR and fluoroscopy technique may not be used simultaneously.

In yet another embodiment of the present invention, the absorbtion of labelled or unaltered porphyrins by atheromatous plaques may be enhanced by binding to the porphyrin some antibody specific to a component of the plaques. Monoclonal antibodies would be particularly useful in this technique due to their extreme specificity. The major component of the plaques is smooth muscle cells. This is also a component of the normal blood vessel wall but it is covered by endethelial cells in the normal vessels. The abnormal endothelium covering the atheromatous plaques appears to allow porphyrins to penetrate more easily than does the normal endothelium lining the blood vessels. In the case of smooth muscle cells, the antibody would probably actually be directed against the myosin. Other components of the plaques which could serve as antigenic targets include the elastic elements, collagen, and lipids.

Although this invention has been described with reference to specific embodiments, it is understood that modifications and variations may occur to those skilled in the art. It is intended that all such modifications and variations be included within the scope of the appended claims.

What is claimed is:

1. A method for diagnosing atherosclerosis, said method comprising:
   injecting a porphyrin solution into the blood vessels to be examined;
   detecting the quantity of porphyrins absorbed by tissues in the blood vessels; and
   contrasting the quantity of porphyrins in different areas of the blood vessels to determine location, size, and quantity of athermatous plaques.

2. The method of claim 1 wherein the porphyrins are radiolabeled.

3. The method of claim 1 wherein a radio-opaque material is bound to the porphyrins.

4. The method of claim 1 wherein a metal is bound to the porphyrin.

5. The method of claim 1 wherein the preferential absorbtion of porphyrins by atheromatous plaques is detected by illuminating the plaques with ultraviolet light and detecting the fluorescence.

6. The method of claim 4 wherein the preferential absorbtion of porphyrins by atheromatous plaques is detected by nuclear magnetic resonance spectroscopy.

7. The method of claim 2 wherein the preferential absorbtion of porphyrins by atheromatous plaques is detected by radionuclide scintillation techniques.

8. The method of claim 3 wherein the preferential absorbtion of X-rays by porphyrins is detected.

9. The method of claim 2 wherein the preferential absorbtion of porphyrins is detected by Positron Emission Tomography.

10. The method of claim 1 wherein an antibody specific for a component of the atheromatous plaques is bound to the porphyrins.

* * * * *